Figure 1:
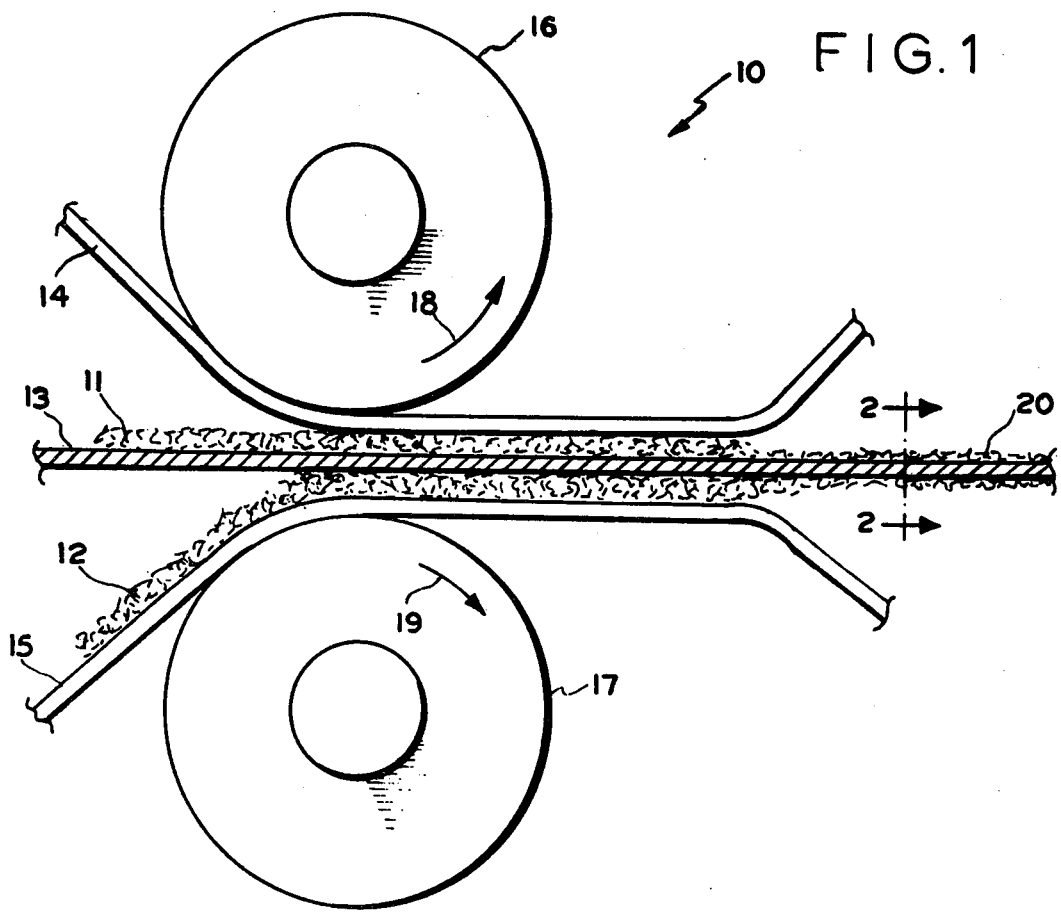

United States Patent [19]
Porta et al.

[11] 4,145,355

[45] Mar. 20, 1979

[54] PROCESS FOR PRODUCING ETHYLENE OXIDE

[75] Inventors: Paolo D. Porta; Angelo Cantaluppi; Bruno Ferrario; Paolo Montalenti, all of Milan, Italy

[73] Assignee: SAES Getters S.p.A., Milan, Italy

[21] Appl. No.: 501,205

[22] Filed: Aug. 28, 1974

Related U.S. Application Data

[62] Division of Ser. No. 249,772, May 3, 1972, Pat. No. 3,856,709.

[30] Foreign Application Priority Data

Apr. 29, 1972 [IT] Italy .............................. 23727 A/72

[51] Int. Cl.$^2$ .......................................... C07D 301/10
[52] U.S. Cl. .............................................. 260/348.34
[58] Field of Search ........................ 260/348.5, 348.34

[56] References Cited

U.S. PATENT DOCUMENTS 3,857,680  12/1974  Porta et al. ................... 260/348.5 R

*Primary Examiner*—Norma S. Milestone

*Attorney, Agent, or Firm*—Littlepage, Quaintance, Murphy, Richardson and Webner

[57] ABSTRACT

A method of producing a substrate having a particulate coating of high surface area to mass ratio, said method comprising in sequence the steps of:
- I. disposing between a substrate and an intermediate body a mixture comprising:
  - A. hard particles which are harder than the substrate and are harder than the intermediate body, and
  - B. soft particles which are softer than the hard particles and are softer than the substrate,
- II. compressing the substrate and intermediate body, with particles therebetween whereby the intermediate body pushes the hard particles into the substrate, and
- III. removing the intermediate body from the particles leaving the hard particles embedded in the substrate and the soft particles adhering to the substrate.

The coated substrates produced by the process of the present invention find utility as catalytic devices to accelerate or retard chemical reactions.

1 Claim, 2 Drawing Figures

U.S. Patent    Mar. 20, 1979    4,145,355

PROCESS FOR PRODUCING ETHYLENE OXIDE

CROSS REFERENCE TO RELATED APPLICATIONS

This application is a division of application Ser. No. 249,772 filed May 3, 1972, and now U.S. Pat. No. 3,856,709, issued Dec. 24, 1974.

Processes have been described for producing substrates having hard metallic particles embedded therein. See the above-identified grandparent and Italian Pat. No. 746,551 issued Feb. 1, 1967. However, heretofore it has been thought that such processes were limited to those wherein the particles were harder than the substrate. Although there are many advantages to such processes such as (1) the absence of a binder, (2) the ability to practice the process at ambient temperatures, (3) the use of rolls while avoiding wear of the rolls and (4) the production of a structure having a higher surface area to mass ratio, these processes require that the particles be harder than the substrate. See U.S. Pat. No. 3,652,317.

It is therefore an object of the present invention to provide a method for producing a substrate having thereon a coating of particles which are softer than the substrate.

Another object is to provide an improved method which does not require the use of a binder; can be practiced at ambient temperatures; and employs rolls which are not subject to wear.

Yet another object is to provide an improved method for producing a coated substrate such as those suitable to be used as catalytic devices, getter devices, or capacitors.

Figure 2:
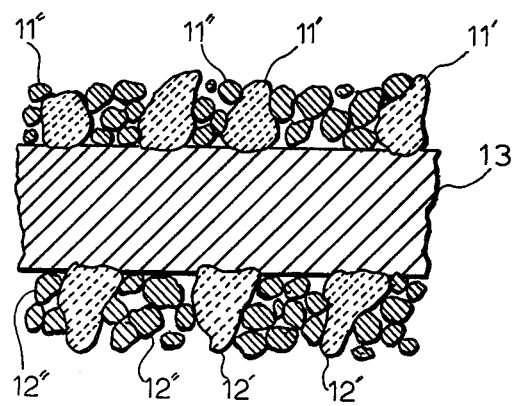

Additional objects and advantages of the present invention will be apparent to those skilled in the art by reference to the following detailed description thereof and drawings wherein:

FIG. 1 is a schematic representation of an apparatus suitable for practicing the method of the present invention; and FIG. 2 is a cross-sectional view with an enlargement of approximately 300 diameters of the structure produced by the process of the present invention. FIG. 2 is taken along line 2—2 of FIG. 1.

In accordance with the present invention there is provided a method of producing a substrate having a particulate metallic coating of high surface area to mass ratio and usually greater than 2 cm$^2$/mg. The method comprises in sequence the steps of:

I. disposing between a substrate and an intermediate body a mixture comprising:
   A. hard particles which are harder than the substrate and are harder than the intermediate body, and
   B. soft particles which are softer than the hard particles and are softer than the substrate.

II. compressing the substrate and intermediate body, with particles therebetween whereby the intermediate body pushes the hard particles into the substrate; and III. removing the intermediate body from the particles leaving the hard particles embedded in the substrate and the soft particles adhering to the substrate.

Referring now to the drawings and in particular to FIG. 1, there is shown an apparatus 10 suitable for practicing the process of the present invention. In the practice of this process mixtures 11 and 12 of hard and soft particles are disposed respectively between a substrate 13 and an upper intermediate body 14 and the substrate 13 and a lower intermediate body 15. Most conveniently the particle mixture 11 is placed on the substrate 13 whereas the particle mixture 12 is placed on the lower intermediate body 15 to form a composite structure which is passed between the nip of two rolls 16 and 17 rotating respectively in the direction of arrows 18 and 19. The apparatus 10 is provided with means for maintaining the distance between the rolls less than the combined thickness of the substrate 13, particles 11 and 12, and intermediate bodies 14 and 15. In the preferred embodiment wherein the intermediate bodies 14 and 15 are work-hardenable the rolls 16 and 17 press the intermediate bodies 14 and 15 with a force such that the intermediate bodies 14 and 15 undergo plastic deformation with concurrent work-hardening while effectively pressing the hard particles in the mixtures 11 and 12 against the substrate 13 without substantially reducing the total surface area of the soft particles in the mixtures 11 and 12.

The entire composite structure then leaves the nip between rolls 16 and 17 with the intermediate bodies 14 and 15 adhering to the particle mixtures 11 and 12 which are attached to the substrate 13. The intermediate bodies 14 and 15 are then removed leaving behind the coated substrate 20. By virtue of the herein described relationship in hardness between the particles in the mixtures 11 and 12, the substrate 13 and the intermediate bodies 14 and 15, both the hard and the soft particles in the mixtures 11 and 12 adhere substantially completely to the substrate 13 rather than to the intermediate bodies 14 and 15. This relationship in hardness is critical to the successful practice of the method of the present invention. For example, if the intermediate bodies 14 and 15 are of the same hardness as the substrate 13, the hard particles in the mixtures 11 and 12 will be randomly embedded in the substrate 13 and the intermediate bodies 14 and 15. On the other hand, if the substrate 13 is harder than the intermediate bodies 14 and 15 the hard particles will preferentially embed themselves into the intermediate bodies 14 and 15.

Referring now to FIG. 2, there is shown a substrate 13 having large hard particles 11' and smaller soft particles 11" embedded therein. It can be seen that the composite structure is highly porous with the result that the total surface area of the soft particles 11" are hardly reduced from that originally present in their loose form. This structure is characteristic of products produced by the process of the present invention employing an intermediate body. The underside of the substrate 13 similarly contains hard particles 12' and soft particles 12". In one embodiment of the present invention, the hard particles 11', 12' are alumina, whereas the soft particles 11", 12" are silver.

The hard particles can be of widely varying particle sizes but are generally those which pass through a U.S. standard screen of 10 mesh per inch and are preferably those which pass through a U.S. standard screen of 100 mesh per inch and are retained on a screen of 600 mesh per inch. The soft particles must pass through a screen of 50 mesh per inch, preferably pass through a screen of 100 mesh per inch and ideally pass through a screen of 200 mesh per inch. However, the soft particles are generally smaller than the hard particles. There is virtually no minimum size for the soft particles. In fact, the smaller the particles the greater their surface area. This is especially advantageous when the resultant structure is intended to be a catalyst. However, the size of the soft particles is generally ½ to 1/10000 and preferably 1/10 to 1/5000 that of the hard particles. During the compressing step this permits the hard particles to maintain separation between the intermediate body and the substrate such that they do not squash the soft particles with a consequent undesirable reduction in their surface area.

Broad and preferred ranges of Vickers hardness for the intermediate body, the particles and the substrate are given in the following table:

| Component | Vickers Hardness | |
|---|---|---|
| | Broad Range (kg/mm$^2$) | Preferred Range (kg/mm$^2$) |
| Intermediate body | 10–600 | 100–300 |
| Hard particles | 100–∞ | 200–800 |
| Soft particles | 0.1–200 | 1–100 |
| Substrate | 1–400 | 10–200 |

The values given in this table are non-limiting in the sense that specific values within the above ranges must be chosen while maintaining the herein-described hardness relationship. In a preferred embodiment of the present invention the intermediate body has a Vickers hardness at least 50 and preferably at least 100 kg/mm$^2$ less than the hard particles; and the substrate has a Vickers hardness of at least 40 and preferably at least 80 kg/mm$^2$ less than the intermediate body. The soft particles are generally no harder than the substrate and are usually softer than the substrate.

The soft particles can be those of any metal, or material. In that preferred embodiment wherein the resultant structures are catalytic structures the soft particles are those of a catalytic metal. Of course the catalytic metal is chosen with respect to the chemical reaction to be catalyzed depending upon chemical process considerations forming no part of this invention. However, representative examples of suitable catalytic metals include among others, silver, gold, platinum, mixtures thereof and alloys thereof with one another and with other metals.

In the broadest aspects of the present invention, the hard particles can either be metals or non-metals, however, non-metals are preferred. When the resultant structure is a catalytic device, the hard particles must not inhibit the chemical reaction. Examples of suitable metals include among other zirconium, vanadium, tantalum, and titanium. Examples of suitable non-metals include among others silicon carbide, silicon nitride, boron nitride, silica, and alumina which is preferred. The refractory metal oxides represent a preferred subgenus of non-metallic hard particles.

The weight ratio of hard to soft particles can vary widely as long as the advantages of the present invention are realized. However this ratio is generally between 1:20 and 4:1 and preferably between 1:10 and 1:1. At appreciably lower ratios there are insufficient hard particles present to maintain separation of the substrate and the intermediate body. This results in undesirable flattening or squashing of the soft particles with a concurrent undesirable reduction in their total surface area. A further undesirable effect of low ratios is decreased adhesion of the soft particles to the substrate. At appreciably higher ratios the total surface area of the soft particles is reduced simply because fewer of them are present.

The substrate and the intermediate bodies can be of any metal which has the herein described hardness relationship. Examples of suitable metals include among others, soft iron, steel, aluminum, and stainless steel. It must be emphasized that the chemical nature of the elements making up the alloys employed as substrates and intermediate bodies is not critical. In fact, it is conceivable that alloys of identical chemical composition can be employed as both provided that they have differing hardness. However the substrate must not inhibit the catalytic reaction. As is apparent to those skilled in the art, differing hardness can be imparted by conventional metallurgical techniques such as head treatment, cold rolling and the like.

The invention is further illustrated by the following examples in which all parts and percentages are by weight unless otherwise indicated. These non-limiting examples are illustrative of certain embodiments designed to teach those skilled in the art how to practice the invention and to represent the best mode contemplated for carrying out the invention.

EXAMPLES 1

This example illustrates the method of the present invention wherein the resulting structure is a catalytic device.

Referring to FIG. 1, a mixture of finely divided particles of alumina and silver in a weight ratio of 3:7 are placed on each side of an aluminum substrate 0.010 inches thick. The alumina passes through a screen of 100 mesh per inch and is retained on a screen of 600 mesh per inch. The silver passes through a screen of 400 mesh per inch. The substrate has a Vickers hardness of 90 kg/mm$^2$. Two intermediate bodies of iron having a Vickers hardness of 180 kg/mm$^2$ and a thickness of 0.010 inches are placed on each side of the metal particles and the resultant composite passed between the nip of two rotating rolls. The intermediate body is then removed leaving the hard particles embedded in the substrate and the soft particles adhering to the substrate.

EXAMPLE 2

This example illustrates the use of the catalytic devices of the present invention. The resultant catalytic device of Example 1 functions satisfactorily to increase the reaction rate of the reaction of ethylene with oxygen to produce ethylene oxide.

Although the invention has been described in considerable detail with reference to certain preferred embodiments thereof, it will be understood that variations and modifications can be effected within the spirit and scope of the invention as described above and as defined in the appended claims.

What is claimed is:
1. A process for producing ethylene oxide by exposing a mixture of ethylene and oxygen to a catalytic structure comprising:
   A. an aluminum substrate 0.010 inches thick and having a Vickers hardness of 90 kg/mm$^2$,
   B. hard particles of alumina of a size which passes through a screen of 100 mesh per inch and are retained on a screen of 600 mesh per inch wherein the hard particles have a Vickers hardness of 200 to 800 kg/mm$^2$ and the hard particles are embedded in the substrate,
   C. soft particles of catalytic silver which are softer than the hard particles and are softer than the substrate in a mixture with the hard particles of alumina and of a size such that they pass through a screen of 400 mesh per inch and wherein the weight ratio of alumina to silver is 3:7 and the soft particles in the mixture are adhered substantially completely to the substrate.

* * * * *

UNITED STATES PATENT AND TRADEMARK OFFICE
CERTIFICATE OF CORRECTION

PATENT NO. : 4,145,355

DATED : March 20, 1979

INVENTOR(S) : Paolo della Porta

It is certified that error appears in the above—identified patent and that said Letters Patent is hereby corrected as shown below:

On Front Page of Patent

[19] della Porta et al.

[75] Paolo della Porta

Column 1, line 56, delete "." and insert -- , --.

Signed and Sealed this

Twenty-second Day of January 1980

[SEAL]

Attest:

SIDNEY A. DIAMOND

Attesting Officer

Commissioner of Patents and Trademarks